United States Patent
Zilman et al.

[11] Patent Number: 5,885,433
[45] Date of Patent: Mar. 23, 1999

[54] HEAT SINK PLATE MOUNTING FOR ELECTROPHORESIS UNIT

[75] Inventors: Moisey Zilman, N. Massapequa; Finbarr A. Daly, Woodmere; Vincent R. Prezioso, E. Patchogue, all of N.Y.

[73] Assignee: Savant Instruments, Inc., Holbrook, N.Y.

[21] Appl. No.: 834,193

[22] Filed: Apr. 15, 1997

[51] Int. Cl.⁶ .................................................. G01N 27/28
[52] U.S. Cl. ........................ 204/618; 204/621; 204/616; 204/606
[58] Field of Search .................................. 204/466, 467, 204/616, 618, 621, 606; 435/303.1, 809; 165/185; 269/47

[56] References Cited

U.S. PATENT DOCUMENTS

| | | | |
|---|---|---|---|
| 4,325,796 | 4/1982 | Hoefer et al. | 204/467 |
| 4,610,299 | 9/1986 | Hoover | 165/185 |
| 4,668,362 | 5/1987 | November et al. | 204/467 |
| 4,773,984 | 9/1988 | Flesher et al. | 204/618 |
| 4,898,658 | 2/1990 | Karger et al. | 204/603 |
| 4,911,816 | 3/1990 | Love et al. | 204/614 |
| 5,112,470 | 5/1992 | Sylvester | 204/618 |
| 5,185,071 | 2/1993 | Serwer et al. | 204/457 |
| 5,324,412 | 6/1994 | Kolner | 204/619 |
| 5,637,203 | 6/1997 | Sarrine | 204/616 |

*Primary Examiner*—Krisanne Thornton
*Assistant Examiner*—Theresa T. Snider
*Attorney, Agent, or Firm*—Morrison Law Firm

[57] ABSTRACT

The heat sink plate of an electrophoresis unit is mounted to a fixed support with studs on the heat sink plate received in sleeves secured to the fixed frame. Compression springs encircle the sleeves and interpose between the heat sink plate and the fixed frame so that when clamping of a gel slab sandwich to the electrophoresis unit is made, a flat face of the heat sink plate orients in substantially full planar face-to-face contact with a flat face of a gel slab sandwich plate and can have following movement with the sandwich plate that is a pivoting thereof about at least two orthogonally disposed axes passing through the heat sink plate so that with said following movement, face-to-face contact is uniform across the plates and hence, heat transfer from the gel slab maintained uniform.

8 Claims, 5 Drawing Sheets

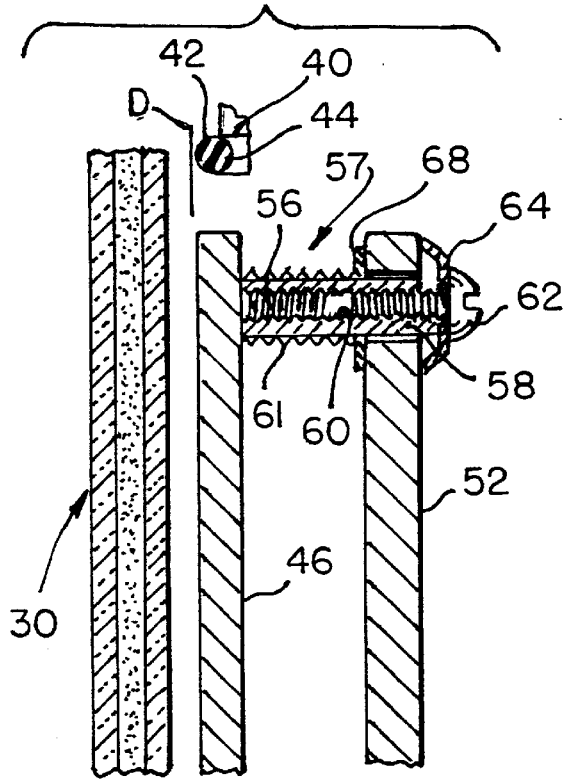
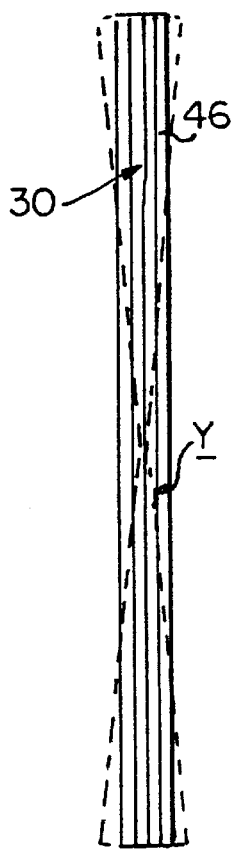
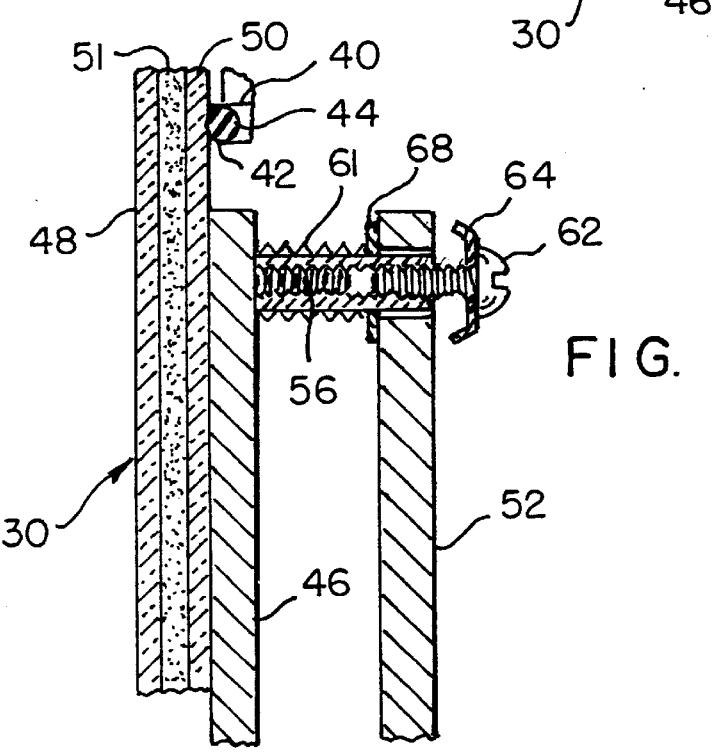

HEAT SINK PLATE MOUNTING FOR ELECTROPHORESIS UNIT

BACKGROUND OF THE INVENTION

The present invention relates to heat sink plate mountings and more particularly, to a mounting for a flat faced heat sink plate against which a flat faced heated body is placed such as is used in an electrophoresis unit.

There are many situations where it is required to withdraw heat from a flat surfaced body to a heat sink so as to avoid heat damage either to the body or to a component within or attached to the body. In some of the situations, the heat sink is provided as an element having a flat surface which is placed in contact with the heated body flat surface.

In this particular situation, it is not unusual that complete face-to-face contact between the two is not achieved over the expanse of each so that in consequence and while measurable heat exchange occurs between the heated body and the heat sink component, uniformity of heat transfer is not present over the contact area of the two elements. The result is creation of hot spots in some locations of interface contact.

Use of a flat heat sink plate in face-to face contact with a flat heated body is practiced in a process for the electrophoretic separation of DNA or RNA. Electrophoresis is a well known molecular biological art practice. An explanation of the practice is found, e.g., in the Background of the Invention description of U.S. Pat. No. 5,324,412.

In the electrophoresis process, a polymerized gel slab is sandwiched between two flat glass or plastic plates, the sandwich is mounted in the electrophoresis unit with its upper and lower ends in contact with electrolyte solutions in respective unit upper and lower reservoirs, a biological sample from which molecules are to be separated is introduced at the top of the gel, and an electric potential is established between the upper and lower reservoir electrolytes.

This results in migration of molecules from the sample through the gel slab from top to bottom, separated molecules becoming visibly discernible in the slab in the course of processing. Ideally, the molecule presence will appear as vertically and horizontally aligned dashed or dotted lines.

In the course of processing heat will be generated in the slab so that heat carry off should be made, this being done by face-to-face engaging one sandwich plate with a heat sink plate. Desirably, heat carry off from the gel slab should be uniform across the slab so that heat condition in the slab would be uniform. Further, if effective uniform heat removal from the slab is present, the slab can be allowed to run hotter since such makes the processing faster.

If pockets of hot or cold spots are created in the slab because there are correspondingly different heat conditions of heat transfer from the slab to the heat sink plate at these locations, the molecule migration speed through the slab will be affected and in consequence, the alignment and more particularly the horizontal alignment of molecule presence is distorted causing so called "smile" and "frown" appearances of the line depictions of the separated molecules which burdens the scientist with trying to correctly match the line or dot associations.

Lack of uniform heat transfer happens because there is lack of uniform face-to-face contact between the respective planar faces of the sandwich plate and the heat sink plate. This can be caused by unequal clamping effect applied to the gel slab sandwich when it is mounted in the electrophoresis unit with clamps, clamps being carried on the unit to clampingly engage the sandwich at side margins of the sandwich. Also, the clamping of the sandwich can make the gel slab thinner at the sides and thicker in the middle so that this can cause heat transfer problems as can warping of the glass plates caused by excessive clamping force and with warping, plate contact with the heat sink plate is reduced.

Clamping of the plate in mounted position is also effected to insure a tight sealing of an upper part of the sandwich against a seal member carried on the unit just adjacent below an edge of an opening in the upper reservoir at which the electrolyte in the upper reservoir is placed in communication with the gel slab, a requirement of the processing. Without a proper such sealing, electrolyte from the upper reservoir could leak out and possibly drip down the sandwich to the lower reservoir wherein it could cause thwarting of the processing.

In an effort to overcome the disadvantages noted above, it is known to attach the heat sink plate to a wall support therefor with interposed elastic links such as rubber plates so that the heat sink plate has some floating movement thought to improve making face-to-face contact between the two better. This practice has not been fully successful. It is difficult with these pads to strike a balance between making full face-to-face contact on the one hand and a proper engagement of the upper reservoir/sandwich plate seal so that if better heat transfer is made more uniform with better plate contact, improper sealing of the reservoir with the sandwich results. If greater clamping pressure is applied to the gel sandwich in quest to seal the reservoir, the sandwich glass easily can be bowed so that the leak potential is magnified in addition to the adverse effect it can have on uniform heat transfer.

Accordingly, it is desirable that an improved mounting for a heat sink plate of an electrophoresis unit be provided so that maximized face-to-face contact of the planar face of the heat sink plate with a sandwich plate of the gel slab sandwich exist while at the same time a sure sealing of the gel slab sandwich with the unit upper reservoir also be present and that the same be made without need for an unusually high clamping force.

OBJECTS AND SUMMARY OF THE INVENTION

Accordingly, it is an object of the invention to provide a mounting for an electrophoresis unit heat sink plate which overcomes the drawbacks of the prior art.

Another object of the invention to provide a heat sink plate mounting which facilitates presentation and maintenance of a planar face of a heat sink plate in substantially full face-to-face contact with a planar face of a sandwich plate of a gel slab sandwich from which heat is being removed thereby to insure that uniform heat transfer from the latter to the former and without creation of any hot or cold spots at locations in the gel slab plate during processing.

It is a still further object of the invention to provide a heat sink plate mounting which effects better sealing between the gel slab sandwich and the upper reservoir.

Briefly stated, there is provided a heat sink plate mounting for an electrophoresis unit in which the heat sink plate is mounted to a fixed frame with plural cooperating paired first and second connector elements carried at locations on the heat sink plate and fixed frame. Compression springs encircle paired first and second connector elements and interpose between the heat sink plate and the fixed frame. When clamping of a gel slab sandwich to the electrophoresis unit is made, a flat face of the heat sink plate orients in substantially full planar face-to-face contact with a flat face of a gel slab sandwich plate. Thus, the heat sink plate can have following movement with the sandwich plate that is a pivoting thereof about at least two orthogonally disposed axes passing through the heat sink plate. With this following movement, face-to-face contact is uniform across the plates and hence, heat transfer from the gel slab maintained uniform.

In accordance with these and other objects of the invention, there is provided a mounting for a heat sink plate having a generally planar face against which a second plate having a like generally planar face and containing heat which is to be removed therefrom can be contactingly juxtaposed. The second plate planar face is engaged against the heat sink plate planar face under clamping force applied to said second plate at opposite side marginal areas of said second plate. The mounting comprises a fixed frame and the heat sink plate has a plurality of first connector elements fixed at a second heat sink plate face opposite to its said generally planar face. The fixed frame has at least a like plurality of second connector elements cooperatively engagable with the first connector elements for supporting the heat sink plate with its second face in front of said fixed frame. Compression springs interpose between the heat sink plate second face and the fixed frame, the compression springs function normally to urge the heat sink plate away from the fixed frame but to yield such under impetus of a clamping force applied to the second plate urging the second plate toward the fixed frame with the second plate in juxtaposed face-to-face contact with the heat sink plate. By this the heat sink plate has following movement with the second plate and planar face-to-face therebetween is maintained. The cooperating first and second connector elements are disposed in an array of such that movement of the heat sink plate is a pivoting thereof about at least two orthogonally disposed axes passing through the heat sink plate.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 5 is a fragmentary elevational view partly in section showing the manner by which the heat sink plate is adjustably mounted so as to allow setting a selected distance between the heat sink plate and the upper reservoir/sandwich plate seal;

FIGS. 6A and 6B are respective top plan and side elevational showings of the manner in which the heat sink plate can pivot to follow movements of the gel sandwich plate to maintain substantially full face-to-face contact therebetween; and FIG. 7 is a view like FIG. 5 but depicting the mounted contact between the heat sink plate and the gel slab sandwich with the latter in processing mounted position.

DETAILED DESCRIPTION OF THE PREFERRED EMBODIMENTS

The heat sink plate mounting is described herein in terms of its use in an electrophoresis unit but it should be understood it is equally useful in other applications wherein it is contemplated that heat be removed from a body having a flat planar surface to a heat sink and considerations allow that a flat plate can or need be used as the heat sink.

Figure 1:
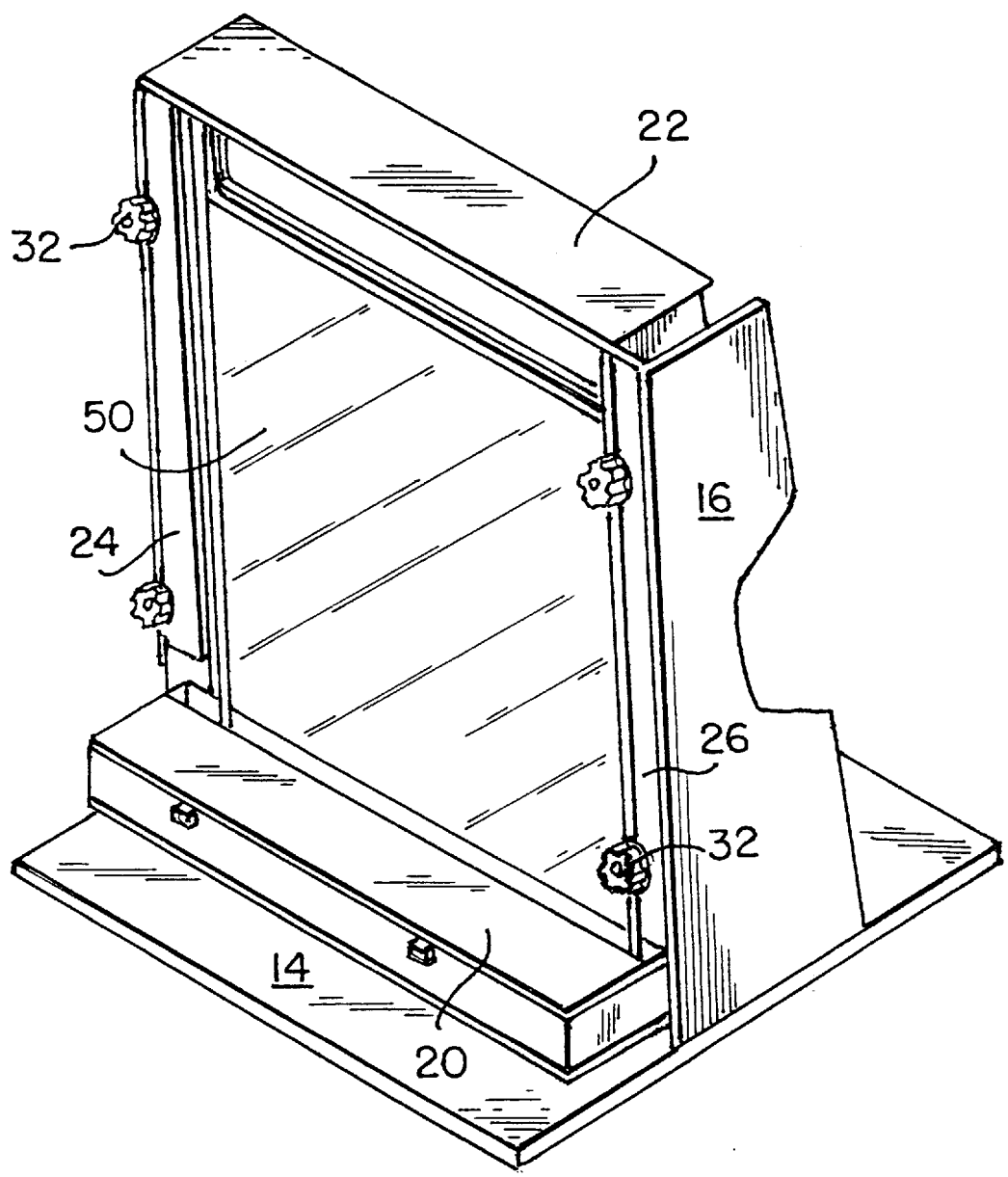
FIG. 1 is a perspective view of a type of electrophoresis unit in which the heat sink plate mounting of the invention readily can be incorporated.
Figure 2:
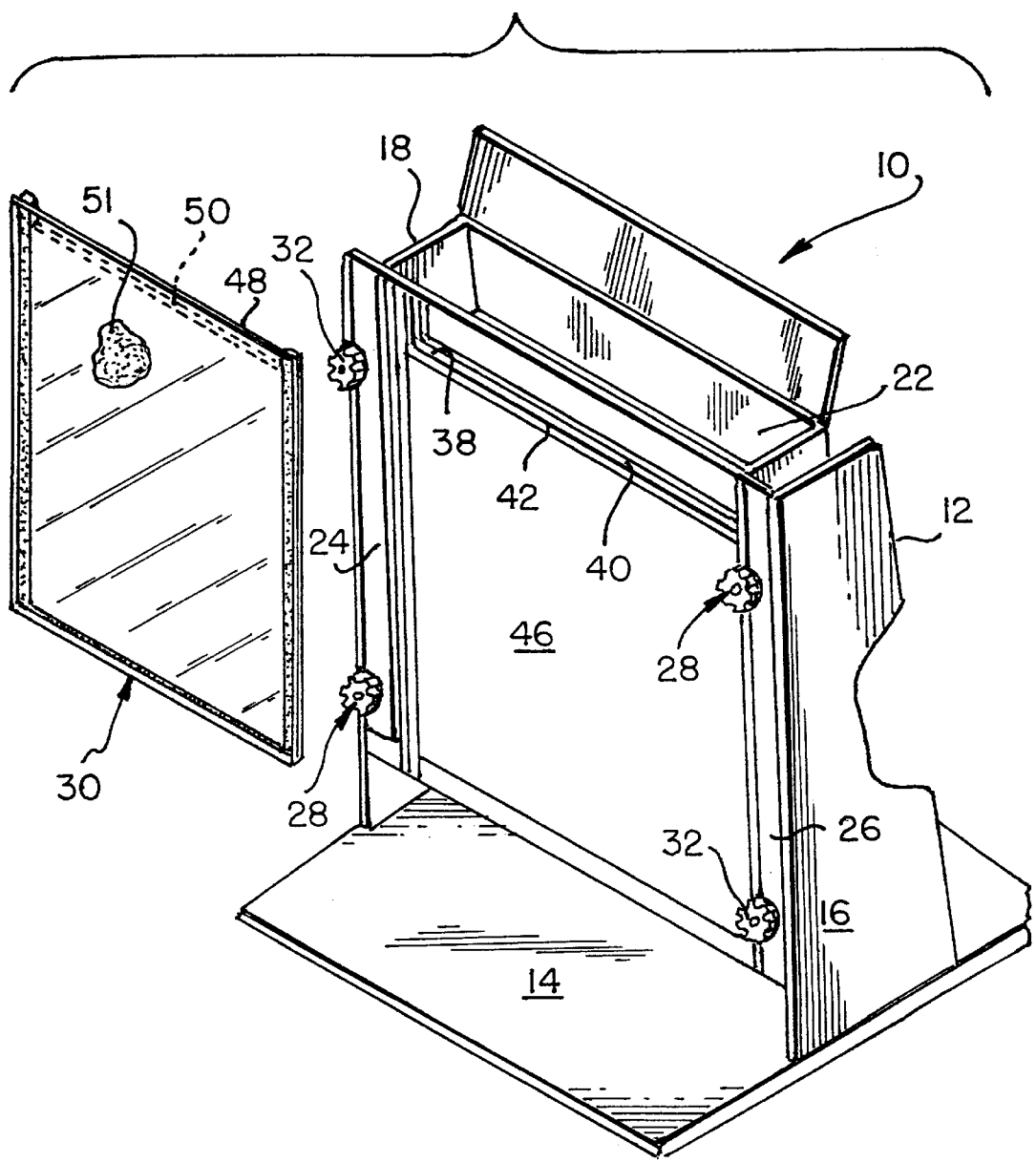
FIG. 2 is a perspective showing of the FIG. 1 electrophoresis unit exploded to show the gel slab sandwich in removed position.

Referring to FIGS. 1 and 2, the electrophoresis unit 10 includes a housing 12 comprised of a base 14, side walls 16, 18, a lower electrolyte reservoir 20, and an upper electrolyte reservoir 22, the reservoir preferably having protective covers. Structure at front sides of the housing can carry gel slab sandwich clamp elements 28 which are used for clamping the gel slab sandwich 30 to the unit and against the hereafter mentioned heat sink plate. The clamp elements 28 can comprise rotatable pressure wheels 32 set over pressure plates 24, 26, swingable clamp arms, cams or any suitable component which can engage the front plate face of the gel slab sandwich and apply clamping force to press a rear plate of the sandwich against the heat sink plate and maintain it in that condition.

Lower reservoir 20 and upper reservoir 22 each hold electrolytic liquids and the upper reservoir is cut away as at 38 to communicate liquid therein with the gel slab of the sandwich. The particulars of how processing is carried out is well known to one skilled in the art.

Adjacent the lower edge 40 of the upper reservoir cutaway 38 and in front thereof is a resilient material seal 42 which a rear plate face of the sandwich engages when the sandwich is clamped in place to effect a sealing of the sandwich mounting to prevent leakage of electrolyte from the upper reservoir, the cutaway best being seen with reference to FIG. 2 while FIG. 1 best shows the clamped mounting of the sandwich on the unit.

Figure 3:
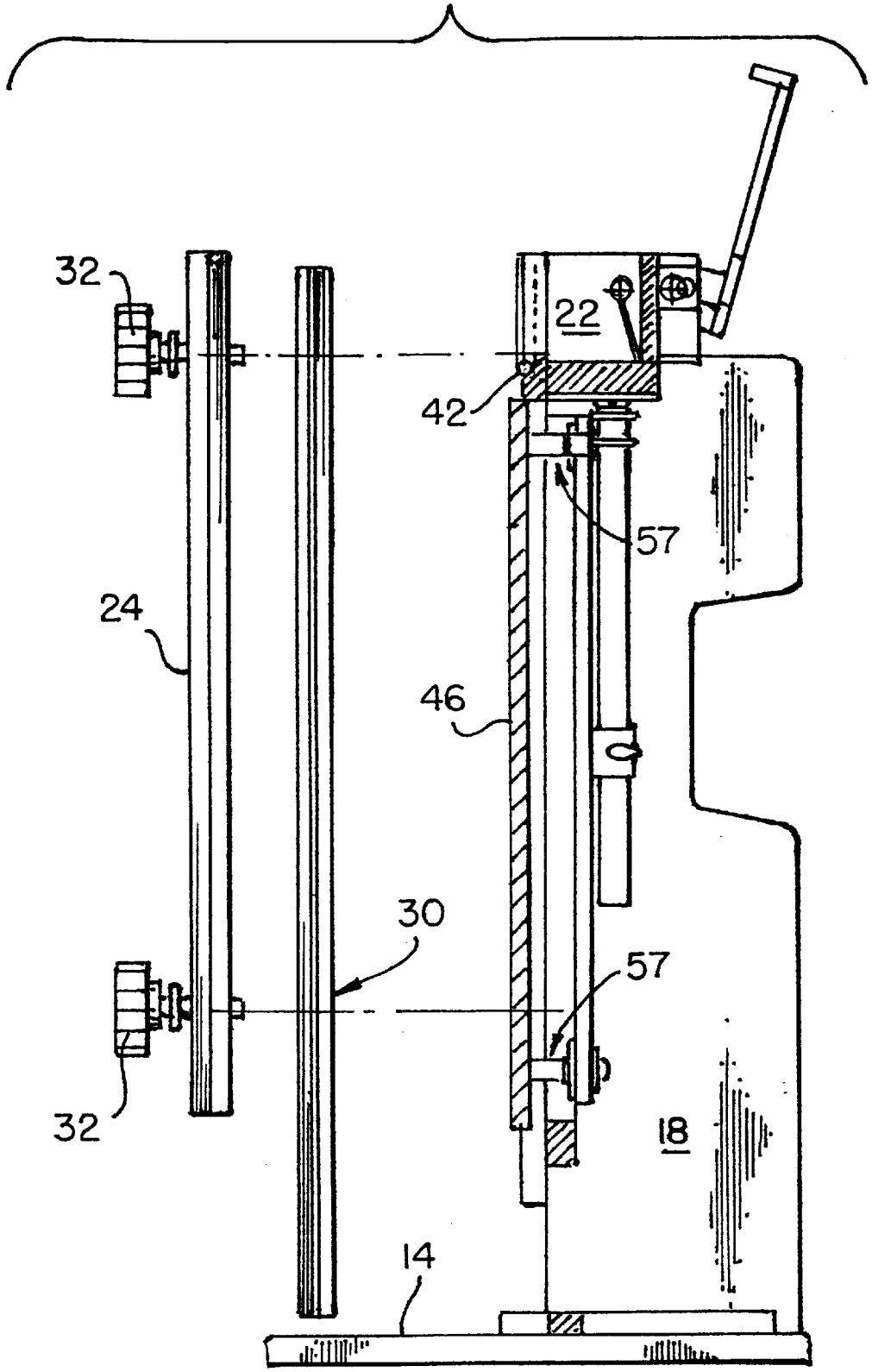
FIG. 3 is a side view of the electrophoresis unit, partly in section and partly exploded so as to show details of the heat sink mounting.

The FIG. 2 depicted seal is depicted as flat faced but it also can be of circular section as shown in FIGS. 3 and 5. A groove 44 (FIG. 5) can be provided in a lower part of the upper reservoir structure to receive the seal 42.

The unit also includes a heat sink plate 46 set centrally in the unit with its side margins underlying the pressure plates 24, 26. The heat sink plate can be of various materials which readily absorb heat being, for example, a metal such as an anodized aluminum or a ceramic. The mounting of the heat sink plate 46 in the unit 10 is given next.

Referring to FIG. 2, the gel slab sandwich 30 comprises front and rear sandwich plates 48, 50 between which is sandwiched the polymerized material gel slab 51. The sandwich plates 48, 50 are of glass or plastic and have generally face, planar plate faces.

Figure 4:
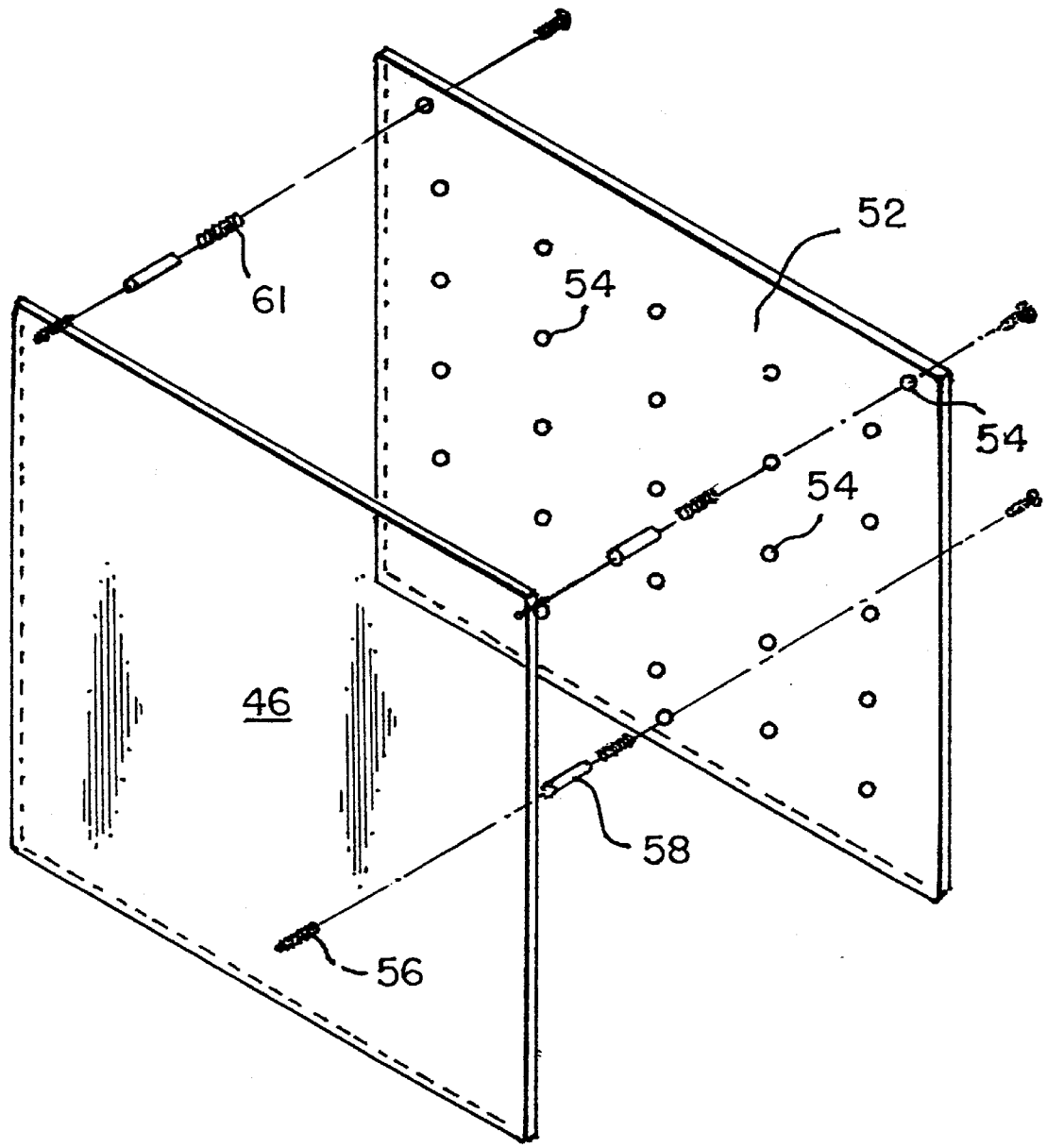
FIG. 4 is a perspective showing in exploded detail of the heat sink plate and the fixed frame of the electrophoresis unit from which the heat sink plate is supported.

With reference to FIGS. 4 and 5, mounting of the heat sink plate now will be given. Unit 10 is provided with a rigidly fixed frame 52 conveniently provided as a panel fixed to or made integral with the side walls 16, 18. The fixed frame 52 has a series of openings 54 by which securement of the heat sink plate thereto can be effected.

Although a large number of openings 54 are seen in the fixed frame, a preferred mounting requires only three be used. Others could be used but three are preferred. Unused openings 54 serve as ventilation holes to aid the overall heat removal function in the unit.

First connector elements, e.g., studs 56, three in number in a preferred embodiment, are located at a rear side of the heat sink plate and can be fixed thereto. These first connector elements 56 are disposed in array such that two are proximal the top of the heat sink plate and the third is proximal the bottom of the heat sink plate. Further, the two top first connector elements providing that the top two first connector elements are located symmetrically with respect to the third. It is also seen that the three first connector elements located on the heat sink plate are at the apices of an equilateral triangle, are laterally spaced close to the respective side margins of the heat sink plate while the third first connector element is centered on the plate between the locations of the top two first connector elements.

The advantage of using the so arranged first connector elements array is that the flatness of presentation for juxtaposed contact of the planar front face of the heat sink plate 46 to the planar face of the rear sandwich plate 50 is best defined with three point mounting.

Supporting of the heat sink plte 46 to the fixed frame 50 can be effected in one manner with cooperatively interengaging second connectors 57 located on the fixed frame 52.

Cylindrical sleeves 58, internally threaded as at 60, pass through opening 54 and a screw 62 is threaded into the sleeve from the rear side of the fixed frame, the screw passing through a washer or a keeper ring 64 loose mounted at the rear side of the fixed frame. Sleeve 58 also is threaded onto the associated stud 56 as shown.

Optionally, a washer 68 is located at the front side of the fixed frame and intervenes sleeve 58 and the flat panel face of the fixed frame. A compression spring 61 loose on the exterior of the sleeve intervenes the rear face of the heat sink plate 46 and the front face of the fixed frame 52.

By rotating screw 62 in one or an opposite direction, the sleeve 58 can be slid in corresponding directions to move the heat sink plate forwardly or rearwardly as desired. Required such movement will be only slight and will be employed when it is desired to set the distance D (FIG. 5) between the front face of the heat sink plate and the front extreme of seal 42 for reason as given next.

Distance D is set with respect to a condition when the gel slab sandwich is not yet mounted in the unit 10. When the gel slab sandwich is inserted in the unit and clamping initiated, face-to-face contact of the heat sink plate 46 with sandwich plate 50 and under clamping pressure the heat sink plate will be pressed rearwardly slightly while planar face-to-face contact conformity ensues. Near the end of clamping movement, the top of the rear face of sandwich plate 50 will engage against seal 42 and on full clamping, proper sealing between the plate 50 and the seal effect to obviate leakage at the reservoir when the latter is filled with electrolyte.

Optimizing the set distance D insures that first, proper heat sink plate/sandwich plate contact is achieved followed by proper sealing contact with the top of plate 50 and seal 42. A distance D of substantially about 0.060 inches is found appropriate for most uses of the depicted type electrophoresis unit of which E-C Apparatus Corporation EC 160 DNA Sequencing System is exemplary.

FIG. 7 shows the juxtaposed contact between the heat sink plate 46 and the gel slab sandwich 30, as well as the compression of seal 42 effected when the sandwich is in the unit in mounted position, the spring 61 having been slightly further compressed from the FIG. 5 showing condition.

When the gel slab sandwich 30 is being mounted in the unit 10 and face-to-face contact established therebetween, the three point mounting and the spring action allows the heat sink plate to pivot about at least two orthogonally disposed axes X and Y as shown in respective FIGS. 6A and 6B or to having such a movement as is a combination of these pivotings. By this, and if there be slight skewing of the rear face of sandwich plate 30 due to unevenness in the applied clamping forces applied at a number of locations on the sandwich plate by the clamp elements, the heat sink plate can float or follow the face of sandwich plate 30 to establish and sustain full face-to-face intimate contact between these components.

Accordingly and because of this face-to-face contact, heat transfer from the gel slab 51 through sandwich plate 50 and into the heat sink plate will be substantially uniform and presence of any hot/cold spots in the gel slab prevented.

While a preferred mounting of the heat sink plate is given above, it is understood that various modifications can be within the scope of the inventive concept disclosed. For example, instead of using studs at the rear face of the heat sink plate, it could have blind threaded bores at the three locations discussed above, and an end of the sleeve 58 could be correspondingly externally threaded so that the sleeves would be screwed to the heat sink plate, or another way would be to press fit the sleeve into bored holes. In such instance, the screw 62 would be the second connector element.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A mounting for a heat sink plate having a generally planar face against which a second plate, the mounting comprising a fixed frame, a heat sink plate having a generally planar face against which a second plate having a like generally planar face and containing heat which is to be removed therefrom by contactingly juxtaposing the second plate planar face against the heat sink plate planar face under clamping force applied to said second plate at opposite side marginal areas of said second plate, said heat sink plate further having a plurality of first connector elements fixed at a second heat sink plate face opposite to its said generally planar face, said fixed frame having at least a like plurality of second connector elements cooperatively engagable with said first connector elements for supporting the heat sink plate with its second face in front of said fixed frame, and compression springs interposed between the heat sink plate second face and the fixed frame, said compression springs functioning normally to urge the heat sink plate away from the fixed frame but to yield such under impetus of a clamping force applied to the second plate urging the second plate toward the fixed frame with the second plate in juxtaposed face-to-face contact with the heat sink plate so that the heat sink plate has following movement with the second plate and planar face-to-face contact therebetween is maintained, the cooperating first and second connector elements being disposed in an array of such that movement of the heat sink plate is a pivoting thereof about at least two orthogonally disposed axes passing through the heat sink plate.

2. The mounting of claim 1 in which a separate compression spring is associated with each first connector element.

3. The mounting of claim 2 in which the first connector elements comprise three in number, two of said first connector elements being at locations on said heat sink second face proximal a first end of said heat sink plate, a third of said first connector elements being located on said heat sink plate second face proximal a second opposite end of said heat sink plate, the second connector elements which engage said three first connector elements being disposed at locations on the fixed frame which align each in a pairing with the location of said first connector elements on the heat sink plate.

4. The mounting of claim 3 in which the two said first connector elements are laterally spaced on said heat sink plate and symmetrically positioned relative to the location of the third first connector element.

5. The mounting of claim 4 in which the first connector elements in said array are located on said heat sink plate at locations which are at the apices of an equilateral triangle.

6. The mounting of claim 2 in which one of the first connector elements and the second connector elements at each paired location includes a sleeve, the sleeve being encircled by the associated compression spring.

7. The mounting for a heat sink plate of claim 1 as embodied in an electrophoresis unit housing, the fixed frame comprising an upright panel at a rear of the housing, the second plate comprising
one sandwich plate of an electrophoresis gel mold received in upright disposition on said housing with the said one sandwich plate at a front side of the heat sink plate, said housing including
an upper reservoir for receiving an electrolyte liquid, the housing carrying a resilient seal located adjacent a lower part of the upper reservoir,
an upper edge of the heat sink plate being located below said seal so that an upper part of said one sandwich plate can when said one sandwich plate is contactingly juxtaposed with clamping force against said heat sink plate, engage against said seal to establish an anti-leakage barrier preventing passage of electrolyte liquid from said upper reservoir to either the planar or second opposite faces of the heat sink plate, the cooperating first and second connector elements being such that at least one is adjustably movable forwardly and rearwardly relatively of the fixed frame so that a disposition of the generally planar face of the heat sink plate in absence of said one sandwich plate of the gel mold being in contact therewith, can be set at a selected distance from a forward extreme of said seal.

8. The mounting of claim 7 in which the said one of the cooperating first and second connector elements is such adjustable as to provide that a disposition of the generally planar face of the heat sink plate can be set at a selected distance from the forward extreme of said seal which is any one in a range of 0 inches up to at least about 0.060 inches.

* * * * *